United States Patent [19]

Saito et al.

[11] Patent Number: 5,283,331
[45] Date of Patent: Feb. 1, 1994

[54] 2-HALOGENO-OXETANOCIN A AND PHOSPHORIC ESTER THEREOF

[75] Inventors: Seiichi Saito, Kashiwa; Akira Masuda, Yono; Masayuki Kitagawa, Urawa; Nobuyoshi Shimada, Tokyo; Jun-ichi Seki, Takasaki; Hiroo Hoshino, Maebashi; Yukihiro Nishiyama, Aichi, all of Japan

[73] Assignee: Nippon Kayaku Kabushiki Kaisha, Tokyo, Japan

[21] Appl. No.: 804,773

[22] Filed: Dec. 9, 1991

[30] Foreign Application Priority Data

Dec. 20, 1990 [JP] Japan ............................. 2-411947
Mar. 1, 1991 [JP] Japan ............................. 3-057754

[51] Int. Cl.$^5$ ................ C07D 473/40; A61K 31/52; C07F 9/09; C07F 7/18
[52] U.S. Cl. ............................. 544/229; 544/244; 544/277
[58] Field of Search .............. 514/266, 81; 564/244, 564/277, 229

[56] References Cited

U.S. PATENT DOCUMENTS

| | | | |
|---|---|---|---|
| 4,199,574 | 4/1980 | Schaeffer | 544/277 |
| 4,743,689 | 5/1988 | Shimada, III | 544/277 |
| 4,918,075 | 4/1990 | Zahler | 544/277 |
| 5,041,447 | 8/1991 | Saito | 544/277 |
| 5,059,690 | 10/1991 | Zahler | 544/277 |

FOREIGN PATENT DOCUMENTS

| | | |
|---|---|---|
| 0254268 | 1/1988 | European Pat. Off. |
| 0291917 | 11/1988 | European Pat. Off. |
| 0294114 | 12/1988 | European Pat. Off. |

OTHER PUBLICATIONS

Yarchoan, *Science*, 245, p. 412 (1989).

Shimada I *The Journal of Antibiotics* vol. XXXIX, 1623–1625 (1986).
Shimada II *The Journal of Antibiotics* vol. XL, 1788–1790 (1987).

*Primary Examiner*—Mark L. Berch
*Attorney, Agent, or Firm*—Nields & Lemack

[57] ABSTRACT

It was found that 2-halogeno-oxetanocin A and 4′-phosphate thereof represented by the following general formula (1):

$$\text{(1)}$$

wherein X represents a halogen atom and R represents a hydrogen atom or a phosphoric acid residue $$-\overset{\overset{\displaystyle O}{\|}}{\underset{\underset{\displaystyle OH}{|}}{P}}-OH$$

or salts thereof exhibit a strong antiviral activity and are useful as an active ingredient of therapeutic drug for viral diseases. Further, it was also found that the compounds of this invention are characterized in that they are not inactivated by adenosine deaminase widely present in living bodies and exhibit a high residual activity.

2 Claims, No Drawings

2-HALOGENO-OXETANOCIN A AND PHOSPHORIC ESTER THEREOF

BACKGROUND OF THE INVENTION

Today, there is no satisfactory therapeutic drug for viral diseases, and development of a new antiviral agent is waited for.

This invention relates to 2-halogeno-oxetanocin A, phosphoric ester thereof and their salts which are expectedly useful as therapeutic drugs for viral diseases.

STATEMENT OF THE PRIOR ART

Oxetanocin is a compound having an antiviral activity, and it is disclosed in Journal of Antibiotics, Vol. 39, No. 11, 1623-25 (1986), EP-A2-0182315, etc. Its derivatives are also disclosed in Journal of Antibiotics, Vol. 40, No. 12, 1788-90 (1987).

SUMMARY OF THE INVENTION

The present inventors conducted extensive studies with the aim of solving the above-mentioned problem. As the result, it was found that 2-halogeno-oxetanocin A and its phosphoric ester represented by the following general formula (1):

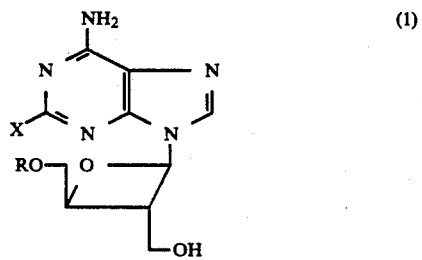

wherein X represents halogen atom and R represents hydrogen atom or phosphoric acid residue

or their salts exhibit an intense antiviral activity and are useful as active ingredient of therapeutic drugs for viral diseases. Further, it was found that the compounds of this invention are characterized in that they are not inactivated by adenosine deaminase which is extensively found in living bodies, so that they exhibit a high residual activity.

DETAILED DESCRIPTION OF THE INVENTION

As used in this invention, the term "halogen atom" inclusively means fluorine, chlorine, bromine and iodine. The compounds represented by general formula (1) form salts with an acid or a base. That is, 2-halogeno-oxetanocin A forms a salt with an acid, and 2-halogeno-oxetanocin A phosphate forms a salt with a base. The acid and base for forming these salts may be anything so far as they are pharmacologically acceptable. Preferable examples of the acid include hydrochloric acid, sulfuric acid, phosphoric acid and the like. Preferable examples of the base include bases giving alkali metal salts such as NaOH, KOH and the like, and triethylamine and the like.

Specific examples of the compound of this invention represented by general formula (1) are shown below:

Compound No. 1: 2-Fluoro-oxetanocin A (2-F-OXT-A)
Compound No. 2: 2-Chloro-oxetanocin A (2-Cl-OXT-A)
Compound No. 3: 2-Bromo-oxetanocin A (2-Br-OXT-A)
Compound No. 4: 2-Iodo-oxetanocin A (2-I-OXT-A)
Compound No. 5: 2-Fluoro-oxetanocin A 4'-phosphate (2-F-OXT-AMP)
Compound No. 6: 2-Chloro-oxetanocin A 4'-phosphate (2-Cl-OXT-AMP)
Compound No. 7: 2-Bromo-oxetanocin A 4'-phosphate (2-Br-OXT-AMP)
Compound No. 8: 2-Iodo-oxetanocin A 4'-phosphate (2-I-OXT-AMP)

The method for synthesizing the compounds of this invention, namely 2-halogeno-oxetanocin A and 4'-phosphoric esters thereof, is mentioned below.

A. Synthesis of 2-Halogeno-oxetanocin A

2-Halogeno-oxetanocin A is synthesized by using 2-amino-oxetanocin A represented by formula, which is a known compound disclosed in Japanese Patent Application Kokai No. 1-100192; EP-A-0 291 017), as a starting material. Its synthetic route is shown in FIG. 1.

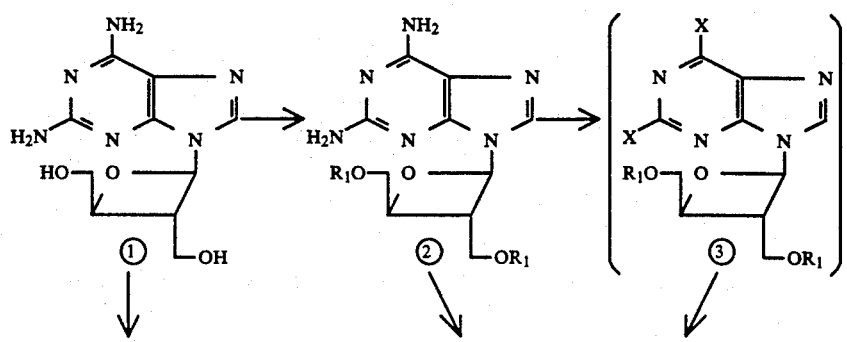

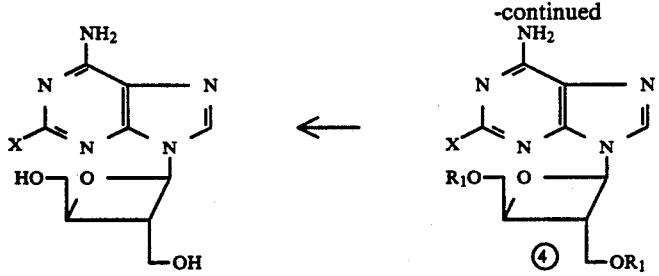

X= F: Compound No. 1
X= Cl: Compound No. 2
X= Br: Compound No. 3
X= I: Compound No. 4

FIG. 1: Syntheses of 2-Halogeno-oxetanocin A

1). Synthesis of 2-F-OXT-A

2-Amino-oxetanocin A is dissolved into aqueous acetic acid and reacted with sodium borofluoride in the presence of an alkali metal nitrite such as sodium nitrite or potassium nitrite. By this procedure, Compound No. 1 can be obtained directly.

In this reaction, the reaction temperature of $-50°$ C. to $20°$ C., preferably $-30°$ C. to $10°$ C. The reaction time is 5 minutes to 4 hours, preferably 10 minutes to 2 hours.

Otherwise, 2-F-OXT-A can be synthesized by the following method, too. Thus, the hydroxyl groups of sugar moiety of 2-amino-oxetanocin A are protected with acyl group or the like to obtain a compound of formula ② wherein $R_1$ is a protecting group. Then, this compound is dissolved into pyridine or the like, and fluorine is selectively introduced into the C-2 position by using hydrogen fluoride/pyridine or the like in the presence of t-butyl nitrite to obtain a compound represented by formula ③ wherein $R_1$ is a protecting group. Subsequently, it is hydrolyzed with an aqueous solution of alkali to eliminate the protecting group. Thus, 2-F-OXT-A (Compound No. 1) is obtained.

As examples of the protecting acyl group, optionally substituted lower alkylcarbonyl groups such as acetyl, chloroacetyl and trichloroacetyl groups, benzoyl groups and the like can be used. Usually, however, it may be acetyl group.

Recommendably, the hydrolysis is carried out by using an alkaline solution such as aqueous solution of ammonia, alkali hydroxide (NaOH, KOH, etc.) and the like at a temperature of $5°$ to $50°$ C., preferably 10 to $40°$ C., for a period of 30 minutes to 48 hours, preferably 1 to 24 hours.

2) Syntheses of 2-Cl-OXT-A, 2-Br-OXT-A and 2-I-OXT-A

2-Cl-OXT-A (Compound No. 2), 2-Br-OXT-A (Compound No. 3) and 2-I-OXT-A (Compound No. 4) are synthesized by using 2-amino-oxetanocin A represented by formula ① (known substance) as a starting compound.

Steps of the syntheses are briefly explained below.

Step 1 (formula ① to formula ②): This is a step for protecting the two primary hydroxyl groups and enhancing the solubility of the substance into the solvent used in Step 2.

As the protecting group of Compound ② ($R_1$ in formula ②), tri($C_1$–$C_{10}$ hydrocarbon)-silyl groups such as trimethylsilyl, t-butyldimethylsilyl, dimethylthexylsilyl and t-butyldiphenylsilyl; acyl groups including optionally substituted lower alkylcarbonyl groups (as the substituent, halogen, lower alkoxy, benzoyl and the like can be used) such as acetyl, chloroacetyl, trichloroacetyl, methoxyacetyl, pivaloyl, phenoxyacetyl, trityloxyacetyl and the like and acyl groups such as benzoyl and the like; and optionally substituted lower alkyl groups including unsubstituted lower alkyl groups such as t-butyl and the like and substituted lower alkyl groups such as trityl, monomethoxytrityl, dimethoxytrityl and the like can be used.

The above-mentioned protecting groups can be introduced according to known methods. Preferably, a protecting group which can be effectively eliminated afterward should be selected.

Step 2 (formula ② to formula ③): This is a step for converting the amino groups at C-2 position and C-6 position of the purine ring to halogen atoms. When the reaction is an iodination, it is carried out in methylene iodide; when the reaction is a bromination, it is carried out in tribromomethane; and when the reaction is a chlorination, it is carried out in carbon tetrachloride; and all these reactions are carried out in the presence of a nitrous acid compound. As said nitrous acid compound, alkyl nitrites such as isoamyl nitrite, sodium nitrite and the like are preferable. These reactions are carried out at a temperature of 20 to $120°$ C., preferably $40°$ to $100°$ C., for a period of a few minutes to 10 hours, preferably 10 minutes to 1 hour.

Step 3 (formula ③ to formula ④): This is a step for converting the halogeno group at C-6 position to the amino group. Thus, each of the dihalides is dissolved in saturated methanolic ammonia and allowed to stand in an ampoule at a temperature of $0°$ to $50°$ C., preferably ambient temperature, over a period of 2 to 48 hours, preferably 5 to 24 hours, whereby the intended amination can be carried out.

Step 4 (formula ④ to 2-halogeno-oxetanocin A): This is a step for eliminating the protecting group $R_1$. When $R_1$ is an acyl group, Step 4 is unnecessary because it is eliminated in the course of amination of Step 3. When $R_1$ is a tri($C_1$–$C_{10}$ hydrocarbon)-silyl group, it can be eliminated with fluoride ion (for example, with n-tetrabutylammonium fluoride) or under an acidic condition (for example, with hydrochloric acid). Preferably, it is eliminated with n-tetrabutylammonium fluoride in tetrahydrofuran. This reaction is carried out at a temperature of $5°$ to $50°$ C., preferably ambient temperature, for a period of 5 minutes to 3 hours, preferably 10 minutes to 2 hours.

Additionally speaking, 2-Cl-OXT-A (Compound No. 2) and 2-Br-OXT-A (compound No. 3) can be synthesized via another synthetic route, too. That is, it can be obtained by selectively halogenating the C-2 position of the compound of formula ② ($R_1$ is a protecting group)

to obtain compounds of formula ④ (R₁) is a protecting group), followed by eliminating the protecting group from the latter according to Step 4 mentioned above.

As the protecting groups R₁ adoptable in the second synthetic route mentioned above, tri(C₁-C₁₀ hydrocarbon)-silyl groups such as trimethylsilyl, t-butyldimethylsilyl, dimethylthexylsilyl and t-butyldiphenylsilyl can be referred to. In this step, t-butyldimethylsilyl group is usually enough for the purpose of this invention.

The step for selectively chlorinating the C-2 position is carried out by using antimony trichloride and 1,2-dichlorethane in the presence of alkyl nitrite such as t-butyl nitrite, and selectively brominating the C-2 position is carried out by using antimony tribromide and dibromomethane in the presence of alkyl nitrite such as t-butyl nitrite. The reaction is carried out at a temperature of −30° C. to 10° C., preferably −20° C. to 0° C., for a period of 1 to 6 hours, preferably 2 to 5 hours.

3) Syntheses of 2-halogeno-oxetanocin A 4'-phosphates

2-Halogeno-oxetanocin A 4'-phosphates can be synthesized according to the reaction scheme shown in FIG. 2, by using a 2-halogeno-oxetanocin A (Compound No. 1 to No. 4) synthesized according to the method mentioned above.

according to known methods. Preferably, a protecting group which can effectively be eliminated afterward should be selected.

Step 6 (Formula ⑤ to formula ⑥): This is a step for protecting the hydroxymethyl group at the C-2' position and eliminating the protecting group at C-4' position. As the protecting group of the hydroxymethyl group at the C-2' position (R₁ in the formulas), acyl groups are used, of which examples include optionally substituted lower alkylcarbonyl groups (as the substituent, halogen, lower alkoxy, benzoyl and the like can be used) such as acetyl, chloroacetyl, trichloroacetyl, methoxyacetyl, pivaloyl, phenoxyacetyl, trityloxyacetyl and the like and benzoyl groups. Benzyl groups are also included in the examples. The above-mentioned substituents can be introduced according to known methods. A protecting group which can effectively be eliminated afterward should be selected preferably, and in this step acetyl group is preferable. When the protecting group of the hydroxyl group at C-3' position is a tri(C₁-C₁₀ hydrocarbon)-silyl group, it can be eliminated with fluoride ion (for example, with n-tetrabutylammonium fluoride) or under an acidic condition (for example, with hydrochloric acid). Preferably, it is eliminated with n-tetrabutylammonium fluoride in tetrahydrofuran.

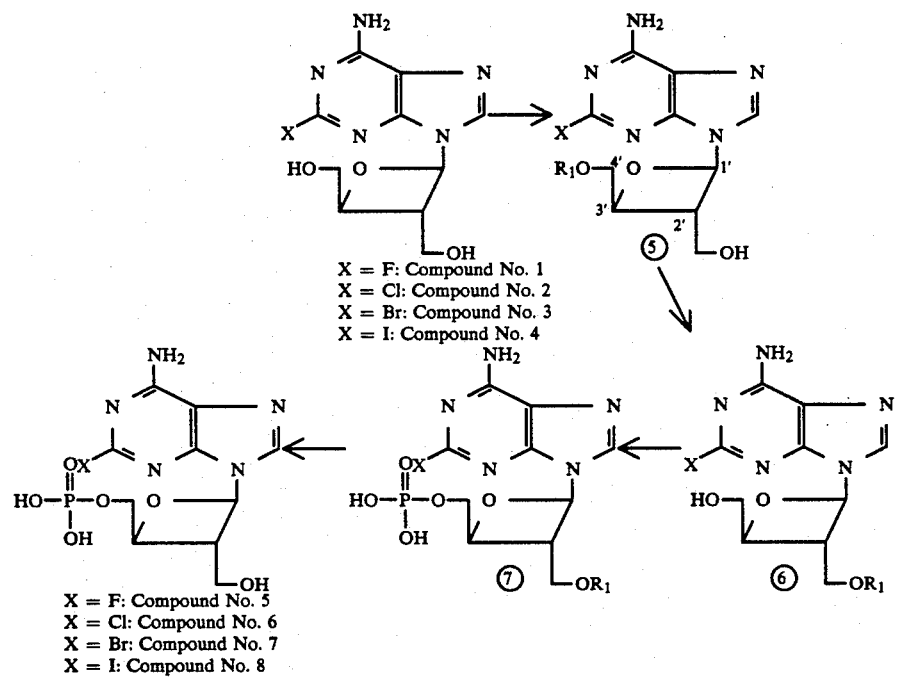

X = F: Compound No. 1
X = Cl: Compound No. 2
X = Br: Compound No. 3
X = I: Compound No. 4

X = F: Compound No. 5
X = Cl: Compound No. 6
X = Br: Compound No. 7
X = I: Compound No. 8

FIG. 2: Syntheses of 2-halogeno-oxetanocin A 4'-phosphates

Steps of the syntheses are briefly explained below.

Step 5 (2-halaogeno-oxetanocin A to formula ⑤): This is a step for protecting the hydroxyl group at the C-2 position.

As the protecting group (R₁ in the formulas), tri(C₁-C₁₀ hydrocarbon)-silyl groups such as trimethylsilyl, t-butyldimethylsilyl, dimethylthexylsilyl and t-butyldiphenylsilyl; and optionally substituted lower alkyl groups including unsubstituted lower alkyl groups such as t-butyl and the like, substituted lower alkyl groups such as trityl, monomethoxytrityl, dimethoxytrityl and the like; and benzyl groups and the like can be used. The above-mentioned protecting groups can be introduced Step 7 (formula ⑥ to formula ⑦ to 2-halogenooxetanocin A 4'-phosphate): This is a step for phosphorylating the hydroxyl group at the C-3' position (formula ⑥ to formula ⑦) and eliminating the protecting group of the hydroxymethyl group at C-2' position (formula ⑦ to 2-halogenooxetanocin A 4'-phosphate). As the phosphorylation reagent, phosphorus oxychloride can be used. The reaction is usually carried out in the presence of a tri(lower alkyl) phosphate such as triethyl phosphate. The reaction is carried out at a temperature of −50° C. to 20° C., preferably −30° C to 10° C., for a period of 10 minutes to 30 hours, preferably 30 minutes to 20 hours.

When the protecting group of the hydroxymethyl group at C-2' position is a group eliminable by hydrolysis such as acyl groups (for example, acetyl group), it is usually eliminated with an aqueous solution of alkali metal hydroxide such as sodium hydroxide, potassium hydroxide and the like or with ammonia. The reaction is carried out at a temperature of 5° to 50° C., preferably ambient temperature, for a period of 30 minutes to 48 hours, preferably 1 to 24 hours.

By the above-mentioned steps, 2-halogenooxetanocin A 4'phosphate can be obtained.

When the compound of general formula (1) is used as a medical drug such as antiviral agent, it is administered either per se or in the form of injection, oral agent, suppository and the like prepared by mixing it with an additive (excipient or carrier). As the excipient and carrier, those pharmacologically acceptable are selected, and their kind and composition are decided with consideration of the route and method of administration. For example, as a liquid carrier, water, alcohol, and animal, vegetable and synthetic oils such as soybean oil, peanut oil, gum oil, mineral oil and the like are used. As a solid carrier, sugars such as maltose, sucrose and the like, amino acids, cellulose derivatives such as hydroxypropyl cellulose and the like, and organic acid salts such as magnesium stearate and the like are used. In the case of injections, the excipient or carrier is preferably selected from physiological salt solution, various buffer solutions, solutions of sugars such as glucose, inositol, mannitol and the like, and glycols such as ethylene glycol, polyethylene glycol and the like It is also possible to prepare the compound of formula (1) into a freezedried preparation together with an excipient such as a sugar (for example, inositol, mannitol, glucose, mannose, maltose, sucrose and the like) or an amino acid (for example, phenylalanine). Such a preparation is dissolved into an appropriate injection solvent such as a liquid for intravinous administration such as sterilized water, physiological salt solution, glucose solution, electrolyte solution, amino acid and the like and then administered.

In these preparations, the content of the compound of this invention varies with the type of preparation. However, it is usually 0.1 to 100% by weight and preferably 1 to 90% by weight. For example, in the case of injections, it is usually recommendable to adjust the content of the compound of this invention to 0.1 to 5% by weight. In the case of oral administration, the compound of this invention is used in the form of tablet, capsule, powder, granule, liquid, dry syrup and the like together with the above-mentioned solid or liquid carrier. In the case of capsule, tablet, granule and powder, the content of the compound of this invention is about 3 to about 100% by weight and preferably 5 to 90% by weight, the remainder being carrier.

The dose of the compound of this invention is decided with consideration of age, body weight and symptoms of the patient and the purpose of the therapy. Generally speaking, the therapeutic dose is 1 to 300 mg/kg.day in non-oral administration and 5 to 500 mg/kg.day in oral administration.

The compounds of this invention are low in toxicity, and all the compounds of this invention are characterized by smallness in the cumulative action of toxicity when administered continually.

The compounds of this invention represented by general formula (1) are made into a preparation in the following manner. For example, 30 parts by weight of 2-halogeno-oxetanocin A hydrochloride or sodium 2-halogeno-oxetanocin A phosphate is diluted with purified water to make the total weight 2,000 parts. After dissolution, the resulting solution is subjected to a sterilizing filtration by the use of Millipore filter GS type. Two grams of the filtrate is taken into a 10 ml vial and freeze-dried to obtain a freeze-dried injection containing 30 mg of a salt of the compound of general formula (1) in one vial.

The compounds of this invention exhibit an antiviral activity against DNA virus or/and RNA virus, and are expected to be useful as an antiviral agent.

Examples of the virus include retroviruses including HIV (Human Immunodeficiency Virus), adenovirus, parvovirus, papovavirus, pox virus, herpes virus, Cytomegalovirus, hepatitis B virus, togavirus, arenavirus and the like.

Particularly Compound No. 1 exhibits an excellent activity against cytomegalovirus, and is expected to be useful as an anti-cytomegalovirus agent. Compound No. 1, Compound No. 2 and Compound No. 6 exhibit excellent activities against HIV, and are expected to be useful as anti-HIV agents.

Next, test examples of this invention are shown below.

TEST EXAMPLE 1

Anti-cytomegalovirus activity was measured in the following manner. Thus, a 35 mm dish having a single layer of human embryo fibroblast was infected with 100 PFU (Plaque Forming Units) of cytomegalovirus (A0169 strain). After adsorption for one hour, it was covered with a layer of a medium [0.5% agarose and 2% fetal calf serum] containing a varied concentration of a compound of this invention. After culturing it for 10 days at 37° C. in a 5% (v/v) carbon dioxide incubator, the number of plaques formed was measured. $ED_{50}$ (50% inhibitory value) calculated therefrom is shown in Table 1.

TABLE 1

| Compound No. | Anti-cytomegalovirus activity $ED_{50}$ ($\mu$g/ml) |
| --- | --- |
| Compound No. 1 | 0.3 |
| Oxetanocin A | 13.0 |

TEST EXAMPLE 2

Anti-HIV activity (anti-Human Immunodeficiency Virus activity) was measured in the following manner. Thus, about 100,000 cells/ml of MT-4 cells were placed in a 24-well tray, and 100 $\mu$l of a solution containing a predetermined quantity of a compound of this invention was added thereto. After culturing it at 37° C. for 2 hours in a 5% (v/v) carbon dioxide incubator, $2.5 \times 10^5$ infection units of HIV was added and cultured for 4 days. Then, a portion of the culture fluid was applied onto a slide glass and immobilized with acetone, after which expression of the viral antigen was tested according to the fluorescent antibody method. As the primary antibody of the fluorescent antibody method, a serum of AIDS patient was used. As the secondary antibody, FITC-labelled anti-human IgG was used.

Cellular denaturation of MT-4 cells caused by the compound of this invention was visually examined under microscope without addition of virus. The result was as shown in Table 2.

TABLE 2

Anti-HIV activities of the compounds of this invention

| Compound No. | Concentration (μg/ml) | Cell denaturation | Expression of viral antigen (%) |
|---|---|---|---|
| Experiment 1 | | | |
| Compound No. 1 | 0.1 | — | 10 |
| | 0.03 | — | 30 |
| | 0.01 | — | 60 |
| Oxetanocin A | 10 | — | 5 |
| | 3 | — | 15 |
| | 1 | — | 70 |
| Experiment 2 | | | |
| Compound No. 2 | 30 | — | 0.1 |
| | 10 | — | 2 |
| | 3 | — | 10 |
| Compound No. 6 | 30 | — | 0.1 |
| | 10 | — | 2 |
| | 3 | — | 13 |
| Oxetanocin A | 30 | ± | 15 |
| | 10 | — | 90 |
| | 3 | — | >90 |

The test were conducted in a comparative manner, using oxetanocin A as a control substance for each of Experiment 1 and 2.

TEST EXAMPLE 3

Sample (0.05 ml) was dissolved into 20 ml of 0.1M phosphate buffer (pH 6.8), and 5 units of adenosine deaminase originated from young calf intestinal mucous membrane (SIGMA Product No. A-1155) was added. While keeping the resulting mixture at a constant temperature of 37° C., its 1 ml portion was sampled out at predetermined intervals. After adding 1 μmole of coformycin and 10-hold diluting the mixture with water, residual percentage of the sample was determined by reverse phase high performance liquid chromatography (column: Senshu Pak ODS-5121-N, 6φ×150 mm; eluent: 0.1M citrate buffer-acetonitrile-methanol (50:2:1); flow rate: 1.8 ml/min.; detection: UV detector, 254 nm). The results are shown in Table 3.

TABLE 3

| Time (min.) | Residual percentage (%) | |
|---|---|---|
| | Oxetanocin A | Compound No. 1, Compound No. 2, Compound No. 5 or Compound No. 6 |
| 0 | 100 | 100 |
| 10 | 85 | 100 |
| 30 | 28 | 100 |
| 60 | 0 | 100 |
| 120 | 0 | 100 |

It is apparent from the above that the compounds of this invention exhibit an excellent antiviral activity against various viruses, they are not inactivated by adenosine deaminase present in living bodies, and they are not strong in cellular toxicity. Accordingly, the compounds of this invention are expected to be effective as therapeutic drugs for viral diseases such as diseases caused by cytomegalovirus, AIDS, and the like.

Next, syntheses and characteristic properties of the compounds of this invention are mentioned in more detail by way of the following examples. In the examples, t-butyldimethylsilyl and acetyl are abbreviated to TBDMS and Ac, respectively.

EXAMPLE 1

Synthesis of 2-fluoro-oxetanocin A (Compound No. 1)

Compound (1) (1.35 g) was dissolved in 80% aqueous acetic acid solution (40 ml). Sodium borofluoride (2.77 g) and sodium nitrite (1.05 g) were added at 0° C. and the reaction mixture was stirred for one hour. The reaction mixture was concentrated under reduced pressure, and the residue was purified by silica gel column chromatography (MERCK silica gel 60, 300 g, eluted with 16% methanol/chloroform), to give Compound No. 1. (0.28 g, 21%).

Compound No. 1

EI-MS (m/z) 269 (M+), 153 (Base+H),
UV ($H_2O$) λmax: 260 nm;
$^1$H-NMR (200 MHz, $Me_2SO$-$d_6$) δppm: 8.64 (1H, s, 8-H), 7.90 (2H, brs; 6NH2), 6.29 (1H, d, 1'-H, J=5.5 Hz), 5.24 (1H, t, 4'-OH), 5.03 (1H, t, 2'-OH), 4.52 (1H, m, 3'-H), 3.73–3.57 (5H, m, 2'-H, 2'-$CH_2$, 4'-Ha,b).

EXAMPLE 2

Synthesis of 2-fluoro-oxetanocin A (Compound No. 1)

2-1 Synthesis of Compound (2) ($R_1$=Ac)

2-Amino-oxetanocin A (Compound (1)) (2 g) was suspended in pyridine (20 ml). Acetic anhydride (1.4 ml) and 4-dimethylaminopyridine (5 mg) were added, and the mixture was stirred overnight at room temperature. The solvent was removed under reduced pressure, saturated aqueous sodium hydrogen carbonate solution (50 ml) was added to the residue, and the product was extracted with chloroform (50 ml×3). The combined organic layer was washed with saturated aqueous sodium chloride solution (50 ml) and dried with sodium sulfate, and then the solvent was evaporated under reduced pressure. The residue was crystallized from ethanol to give Compound (2) ($R_1$=Ac) (2 g).

Compound (2) ($R_1$=Ac)

MS (m/z): 351 (M++1);
UV (MeOH) λmax: 259, 281 nm;
$^1$H NMR ($Me_2SO$-$d_6$): 8.11 (1H, s, 8-H), 6.80 (2H, brs, 6-$NH_2$), 6.22 (1H, d, 1'-H, J=6.2 Hz), 5.88 (2H, brs, 2-$NH_2$), 4.64 (1H, m, 3'-H), 4.50–4.22 (4H, m, 4'-Ha, b, 2'-CHa, b), 4.01 (1H, m, 2'-H), 2.08 (3H, s, Ac), 2.04 (3H, s, AcO).

2-2 Synthesis of Compound (4) ($R_1$=Ac, X=F)

Compound (2) ($R_1$=Ac) (500 mg) was dissolved in a mixture of 70% hydrogen fluoride/pyridine (4 ml) and pyridine (0.7 ml) at −30° C., and then t-butyl nitrite (0.25 ml) was added dropwise and the resulting mixture was stirred for 10 minutes at −30° C. The reaction mixture was poured into crushed ice (10 g)/saturated aqueous sodium carbonate solution (20 ml) and extracted with chloroform (20 ml×3). The combined organic layer was washed with saturated aqueous sodium chloride solution (40 ml), dried with sodium sulfate, and concentrated under reduced pressure. The residue was purified by silica gel column chromatography (MERCK silica gel 60, 80 g, eluted with 4% methanol/chloroform) and crystallized from ethanol to give Compound (4) ($R_1$=Ac, X=F) (302 mg).

Compound (4) ($R_1$=Ac, X=F)

MS (m/z): 354 (M++1);
UV (MeOH) λmax: 260 nm;

¹H NMR (Me₂SO-d₆): 8.48 (1H, s, 8-H), 7.94 (2H, brs, 6-NH2), 6.36 (1H, d, 1'-H, J=6.2Hz), 4.70 (1H, m, 3'-H), 4.49 (1H, dd, 4'-Ha, J=5.6, 12.6Hz), 4.41–4 24 (3H, m, 4'-Hb, 2'-CHa, b), 4.02 (1H, m, 2'-H), 2.07 (3H, s, Ac), 2.04 (3H, s, Ac). 2-3 Synthesis of Compound No. 1

Compound ④ (R₁=Ac, X=F) (254 mg) was dissolved in methanol (10 ml). Concentrated aqueous ammonia (2 ml) was added, the mixture was stirred at room temperature for 2 hours. The precipitate was filtrated and washed with methanol (10 ml) to give Compound No. 1 (163 mg).

Compound No. 1

MS (m/z): 269 (M+), 153 (Base+1);
UV (H₂O) λmax: 260 nm;
¹H NMR (Me₂SO-d₆): 8.64 (1H, s, 8-H), 7.90 (2H, brs, 6-NH2), 6.29 (1H, d, 1'-H, J=5.5Hz), 5.24 (1H, t, 4'-OH), 5.03 (1H, t, 2'-OH), 4.52 (1H, m, 3'-H), 3.73–3.57 (5H, m, 2'-H, 4'-Ha, b, 2'-CHa, b).

EXAMPLE 3

Synthesis of 2-chloro-oxetanocin A (Compound No. 2)

3-1 Synthesis of Compound ② (R₁=TBDMS)

Compound ① (1.78 g) was suspended in N,N-dimethylformamide (50 ml). t-Butyldimethylsilyl chloride (2.21 g) and imidazole (1.14 g) were added, the mixture was stirred at room temperature for 4 hours The reaction mixture was concentrated under reduced pressure. The residue was mixed with saturated aqueous sodium hydrogen carbonate solution and extracted with ethyl acetate The organic layer was washed with saturated aqueous sodium chloride solution, dried with sodium sulfate, and concentrated under reduced pressure. The residue was purified by silica gel column chromatography (MERCK silica gel 60, 240 g, eluted with 4% methanol/chloroform) and crystallized from a mixture of ethyl acetate and hexane to give Compound ② (R₁=TBDMS)=TBDMS) (3.04 g, 92%).

Compound ② (R₁=TBDMS)

EI-MS (m/z): 494 (M+), 437 (M+-t-Bu), 150 (Base+H);
UV (MeOH) λmax: 259, 281 nm;
¹H NMR (200 MHz, CDCl₃) δppm: 8.23 (1H, s, 8-H), 6.35 (1H, d, 1'-H, J=6.0 Hz), 5.49 (2H, brs, 6-NH2), 4.74 (2H, brs, 2-NH2), 4.63 (1H, m, 3'-H), 4.02 (1H, dd, 4'-Ha, J=2, 7, 12.2Hz), 3.92–3.84 (2H, m, 2'-CH2), 3.81 (1H, dd, 4'-Hb, J=2.5, 12.2Hz), 3.63 (1H, m, 2'-H), 0.97–0.88 (18H, m, t-Bu), 0.17–0.06 (12H, m, Me).

3-2 Synthesis of Compound ④ (R₁=TBDMS, X=Cl)

Compound ② (R₁=TBDMS) (144 mg) was dissolved in carbon tetrachloride (10 ml). Isoamyl nitrite (0.59 ml) was added, the mixture was stirred at 60° C. for 2 hours. The reaction mixture was concentrated under reduced pressure. The residue was mixed with methanolic ammonia (30 ml) and allowed to stand in a steel ampoule at room temperature for 20 hours. The reaction mixture thus obtained was concentrated under reduced pressure and the residue was purified by silica gel column chromatography (MERCK silica gel 60, 40 g, eluted with 1% methanol/chloroform) to give Compound ④ (R₁=TBDMS, X=Cl) (78 mg, 52%).

Compound ④ (R₁=TBDMS, X=Cl)

EI-MS (m/z): 458 (M+-t.Bu), 456 (M+-t.Bu), 171 (Base+H), 169 (Base+H);
UV (MeOH) λmax: 262 nm;
¹H NMR (200 MHz, CDCl₃) δppm: 8.54 (1H, s, 8-H), 6.44 (1H, d, 1'-H), J=5.8 Hz), 5.99 (2H, brs, 6-NH2), 4.67 (1H, m, 3'-H), 4.10–3.60 (5H, m, 2'-H, 2'-CH2, 4'-Ha,b), 0.97–0.86 (18H, m, t-Bu), 0.18–0.05 (12H, m, Me).

3-3 Synthesis of Compound No. 2

Compound ④ (R₁=TBDMS, X=Cl) (167 mg) was dissolved in tetrahydrofuran (5 ml), and treated with tetrabutylammonium fluoride (1M in tetrahydrofuran, 0.80 ml) with stirring at room temperature for one hour. The reaction mixture was concentrated under reduced pressure, and the residue was purified by silica gel column chromatography (MERCK silica gel 60. 60 g, eluted with a gradient of 2 to 16% methanol/chloroform) to give Compound No. 2 (78 mg, 84%).

Compound No. 2

EI-MS (m/z): 287 (M+), 285 (M+), 171 (Base+H), 169 (Base+H);
UV (H₂O) λmax: 262 nm;
¹H NMR (200MHz, Me₂SO-d₆) δppm: 8.68 (1H, s, 8-H), 7.88 (2H, brs, 6-NH2), 6.32 (1H, D, 1'-H, J=5.0Hz) 5.27 (1H t 4'-OH). 5.01 (1H, t, 2'-OH), 4.53 (1H, m, 3'-H), 3.73–3.62 (5H, m, 2'-H, 2'-CH2, 4'-Ha,b)

EXAMPLE 4

Synthesis of 2-chloro-oxetanocin A (Compound No. 2)

4-1 Synthesis of Compound ④ (R₁=TBDMS, X=Cl)

The compound ② (R₁=TBDMS) (8 g) synthesized in Example 3, 3-1 and antimony trichloride (7 g) were suspended into 1,2- dichlorethane (200 ml). After adding t-butyl nitrite (8 ml), the mixture was stirred at −10° C. for 3.5 hours. The reaction mixture was poured into crushed ice (100 g)/a saturated aqueous sodium carbonate solution (700 ml) and then extracted with ethyl acetate (600 ml). The organic layer was washed with saturated aqueous sodium chloride solution (500 ml), dried with sodium sulfate, and evaporated under reduced pressure The residue was purified by silica gel column chromatography (MERCK silica gel 60, 300 g, eluted with a gradient of 0 to 1% methanol/chloroform) to give Compound ④ (R₁=TBDMS, X=Cl) (2.96 g).

4-2 Synthesis of Compound No. 2

Compound ④ (R₁=TBDMS, X=Cl) (3 g) was dissolved in tetrahydrofuran (20 ml), and treated with tetrabutylammonium fluoride (1M in tetrahydrofuran, 13 ml) with stirring for one hour at room temperature. The reaction mixture was concentrated under reduced pressure and the residue was purified with Sephadex LH-20 column chromatography (150 ml, eluted with 80% aqueous methanol) to give Compound No. 2 (1.43 g).

Compound No. 2

MS (m/z): 287 (M+), 285 (M+), 171 (Base+1), 169 (Base+1);
UV (H₂P) λmax: 262 nm;
¹H NMR (Me₂SO-d₆): 8.68 (1H, s, 8-H), 7.88 (2H, brs, 6-NH2), 6.32 (1H, d, 1'-H, J=5.0Hz), 5.27 (1H, t, 4'-

OH), 5.01 (1H, t, 2'-OH), 4.53 (1H, m, 3'-H), 3.73–362 (5H, m, 2'-H, 4'-Ha, b, 2'-CHa, b).

EXAMPLE 5

Synthesis of 2-bromo-oxetanocin A (Compound No. 3)

5-1 Synthesis of Compound ④ ($R_1$=TBDMS, X=Br)

Compound ② ($R_1$=TBDMS) synthesized in Example 3 (217 mg) was dissolved in tribromomethane (10 ml). After adding isoamyl nitrite (0.59 ml), the mixture was stirred at 70° C. for 40 minutes. The reaction mixture was concentrated under reduced pressure. The residue was mixed with methanolic ammonia (30 ml) and allowed to stand in a steel ampoule at room temperature for 20 hours. Then, the reaction mixture was concentrated under reduced pressure, and the residue was purified by silica gel column chromatography (MERCK silica gel 60, 60 g, eluted with 1% methanol/chloroform) to give Compound ④ ($R_1$=TBDMS, X=Br) (113 mg, 46%).

Compound ④ ($R_1$=TBDMS, X=Br)

EI-MS (m/z): 544 ($M^+$-Me), 542 ($M^+$-Me), 502 ($M^+$-t.Bu), 500 ($M^+$-t.Bu)

UV (MeOH) λmax: 263 nm;

$^1$H NMR 200MHz, CDCl$_3$) δppm: 8.52 (1H, s, 8-H), 6.45 (1H, d, 1'-H, J=6.0 Hz), 6.01 (2H, brs, 6-NH$_2$), 4.68 (1H, m, 3'-H), 4.10–3.79 (4H, m, 2'-CH$_2$, 4'-Ha,b), 3.64 (1H, m, 2'-H), 0.96–0.88 (18H, m, t-Bu), 0.18–0.07 (12H, m, Me).

5-2 Synthesis of Compound No. 3

Compound ④ ($R_1$=TBDMS, X=Br) (103 mg) was dissolved in tetrahydrofuran (3 ml), and treated with tetrabutylammonium fluoride (1M in tetrahydrofuran, 0.50 ml) with stirring at room temperature for 20 minutes. The reaction mixture was concentrated under reduced pressure, and the residue was purified by silica gel column chromatography (MERCK silica gel 60, 60 g, eluted with a gradient of 2 to 16% methanol/chloroform) to give Compound No. 3 (53 mg, 86%).

Compound No. 3

EI-MS (m/z): 331 ($M^+$), 329 ($M^+$), 215 (Base+H), 213 (Base+H);

UV (H$_2$O) λmax: 263 nm;

$^1$H NMR (200MHz, Me$_2$SO-d$_6$) δppm: 8.65 (1H, s, 8-H), 7.88 (2H, brs, 6-NH$_2$), 6.31 (1H, d, 1'-H, J=5.2 Hz), 5.26 (1H, t, 4'-OH), 5.06 (1H, t, 2'-OH), 4.53 (1H, m, 3'-H), 3.73–3.63 (5H, m, 2'-H, 2'-CH$_2$, 4'-Ha,b).

EXAMPLE 6

Synthesis of 2-iodo-oxetanocin A (Compound No. 4)

6-1 Synthesis of Compound ④ ($R_1$=TBDMS, X=I)

The Compound ② ($R_1$=TBDMS) synthesized in Example 3 (157 mg) was dissolved in methylene iodide (5 ml). After adding isoamyl nitrite (0.43 ml), the mixture was stirred at 80° C. for 10 minutes. After allowing the reaction mixture to cool down to room temperature, methanolic ammonia (40 ml) was added, and the whole mixture was allowed to stand in a steel ampoul at room temperature for 20 hours. Then, the reaction mixture was concentrated under reduced pressure, and the residue was purified by silica gel column chromatography (MERCK silica gel 60, 75 g, eluted with 1% methanol/chloroform) to give Compound ④ (R=TBDMS, X=I) (102 mg, 53%).

Compound ④ ($R_1$=TBDMS, X=I)

EI-MS (m/z): 548 ($M^+$-t.Bu), 261 (Base+H);

UV (MeOH) λmax: 264 nm;

$^1$H NMR (200MHz, CDCl$_3$) δppm: 8.47 (1H, s, 8-H), 6.44 (1H, d, 1'-H, J=5.9Hz), 5.95 (2H, brs, 6-NH$_2$), 4.68 (1H, m, 3'-H), 4.05 (1H, dd, 4'-Ha, J=2.5, 12.3 Hz), 3.87 (2H, m, 2'-CH$_2$), 3.82 (1H, dd, 4'-Hb, J=2.6, 12.3 Hz), 3.60 (1H, m, 2'-H), 0.96–0.89 (18H, m, t-Bu), 0.17–0.08 (12H, m, Me).

6-2 Synthesis of Compound No. 4

Compound ④ ($R_1$=TBDMS, X=I) (102 mg) was dissolved in tetrahydrofuran (3 ml). After adding 1M solution of tetrabutylammonium fluoride in tetrahydrofuran (0.40 ml), the mixture was stirred at room temperature for 20 minutes. The reaction mixture was concentrated under reduced pressure and the residue was purified by silica gel column chromatography (MERCK silica gel 60, 50 g, eluted with a gradient of 2 to 16% methanol/chloroform) to give Compound No. 4 (56 mg, 88%).

Compound NO. 4

EI-MS(m/z): 377 (M+), 261 (Base+H);

UV (H$_2$O) λmax : 265 nm;

$^1$H-NMR (200 MHz, Me$_2$SO-d$_6$) δppm: 8.5 (1H, s, 8-H), 7.76 (2H, brs, 6-NH$_2$), 6.29 (1H, d, 1'-H, J=5.1 Hz), 5.22 (1H, t, 4'-OH), 5.04 (1H, t, 2'-OH), 4.51 (1H, m, 3'-H), 3.73–3.62 (5H, m, 2'-H, 2'-CH$_2$, 4'-Ha,b).

EXAMPLE 8

Synthesis of 2-fluoro-oxetanocin A 4'-phosphate (Compound No. 5)

8-1 Synthesis of Compound ⑤ ($R_1$=dimethylthexylsilyl, X=F)

2-Fluoro-oxetanocin A (Compound No. 1) (314 mg) was suspended in N,N-dimethylformamide (15 ml), and treated with dimethylthexylsilyl chloride (0.27 ml) and imidazole (158 mg) with stirring at room temperature for hours. The reaction mixture was concentrated under reduced pressure, and the residue was partitioned between ethyl acetate (80 ml) and saturated aqueous sodium hydrogen carbonate solution (50 ml). The organic layer was washed with saturated aqueous sodium chloride solution (50 ml), dried with sodium sulfate, and evaporated under reduced pressure. The residue was purified by silica gel column chromatography (MERCK silica gel 60, 50 g, eluted with a gradient of 2 to 3% methanol/chloroform) to give Compound ⑤ ($R_1$=dimethylthexylsilyl, X=F) (110 mg, 23%).

Compound ⑤ ($R_1$=dimethylthexylsilyl, x=F)

MS (m/z): 411 ($M^+$);

UV (MeOH) λmax: 260 nm;

$^1$H-NMR (Me$_2$SO-d$_6$): 8.48 (1H, s, 8-H), 7.91 (2H, brs, 6-NH$_2$), 6.29 (1H, d, 1'-H, J=5.5 Hz), 5.07 (1H, t, 2'-H), 4.54 (1H, m, 3'-H), 4.02 (1H, dd, 4'-Ha, J=5.0, 12.0 Hz), 3.91 (1H, dd, 4'-Hb, J=3.1, 12.0 Hz), 3.72–3.55 (3H, m, 2'-Hb, 2'-CHa, b), 1.60 (1H, sept, thexyl), 0.90–0.75 (12H, m, thexyl), 0.16–0.10 (6H, m, Me).

8-2 Synthesis of Compound ⑥ ($R_1$=Ac, X=F)

Compound ⑤ ($R_1$=dimethylthexylsilyl, X=F) (94 mg) suspended in acetonitrile (10 ml). After adding acetic anhydride (64 μl) and triethylamine (95 μl), the mixture was stirred at room temperature for one hour. The reaction mixture was concentrated under reduced pressure to yield a crude 2'-OAc-3'-0-dimethylthexylsilyl compound. It was dissolved in tetrahydrofuran (3 ml), and treated with tetrabutylammonium fluoride (1M in tetrahydrofuran, 0.3 ml) with stirring at room temperature for 2 hours. The solvent was removed to dryness, and the residue was purified by silica gel column chromatography (MERCK silica gel 60, 15 g, eluted with 4% methanol/chloroform) to give Compound ⑥ ($R_1$=Ac, X=F) (69 mg, 92%).

Compound ⑥ ($R_1$=Ac, X=F)

MS (m/z): 331 (M+);
$^1$H-NMR (Me$_2$SO-d$_6$): 8.60 (1H, s, 8-H), 7.91 (2H, brs, 6-NH$_2$), 6.29 (1H, d, 1'-H, J=6.1 Hz), 5.30 (1H, m, 4'-OH), 4.52 (1H, m, 3'-H), 4.37 (1H, dd, 2'-CHa, J=5.9, 11.6 Hz), 4.26 (1H, dd, 2'-CHb, J=5.4, 11.6 Hz), 3.83 (1H, m, 2'-H), 3.74–3.67 (2H, m, 4'-Ha, b), 2.02 (3H, s, Ac).

8-3 Synthesis of Compound No. 5

Compound ⑥ ($R_1$=Ac, X=F) (20 mg) was suspended in triethyl phosphate (0.6 ml). Phosphorus oxychloride (34 µl) was added under an argon atmosphere at −20° C., and the mixture was stirred at 0° C. for 16 hours. The reaction mixture was neutralized with saturated aqueous sodium carbonate solution (20 ml), and washed thrice with chloroform (15 ml each). The aqueous layer was applied to DEAE-Sephadex A-25 column (carbonate form, 20 ml), washed with water and eluted with a gradient of 0.1 to 0.4M aqueous sodium carbonate solution (250 ml). The homogeneous fractions were pooled, and concentrated under reduced pressure, and the residue, i.e. Compound ⑦ ($R_1$=Ac, X=F), was suspended into methanol (3 ml), mixed with concentrated aqueous ammonia (2 ml) and stirred at room temperature for 3 hours. The reaction mixture was concentrated under reduced pressure, diluted with 1% aqueous sodium chloride solution (40 ml) and passed through a column of active charcoal (5 ml). After washing the column with water, the adsorbed matter was eluted with 80% aqueous methanol (10 ml). The solvent was distilled off from the eluted fraction under reduced pressure to give Compound No. 5 (11 mg, 50%).

Compound No 5

MS (m/z): 350 (M+);
UV (H$_2$O) λmax: 261 nm;
$^1$H-NMR (D$_2$O): 8.74 (1H, s, 8-H), 6.44 (1H, d, 1'-H, J=5.6 Hz), 4.91 (1H, m, 3'-H), 4.19–4.11 (2H, m, 4'-Ha, b), 4.01–3.81 (3H, m, 2'-H, 2'-CHa, b).

EXAMPLE 9

Synthesis of 2-chloro-oxetanocin A 4'-phosphate (Compound No. 6)

9-1 Synthesis of Compound ⑤ ($R_1$=TBDMS, X=Cl)

Compound No. 2 (405 mg) was dissolved in N,N-dimethylformamide (15 ml). tert-Butyldimethylsilyl chloride (257 mg) and imidazole (116 mg) were added, and the mixture was stirred at room temperature for 2 hours. The reaction mixture was concentrated under reduced pressure, and the residue was partitioned between saturated aqueous sodium hydrogen carbonate solution (60 ml) and ethyl acetate (80 ml). The organic layer was washed with saturated aqueous sodium chloride solution (60 ml), dried with sodium sulfate, and evaporated under reduced pressure. The residue was purified by silica gel column chromatography (MERCK silica gel 60, 100 g, eluted with 2% methanol/chloroform) to give Compound ⑤ ($R_1$=TBDMS, X=Cl) (73 mg).

Compound ⑤ ($R_1$=TBDMS X=Cl)

UV (MeOH) λmax: 262 nm;
EI-MS (m/z): 401 (M+), 399 (M+);
$^1$H-NMR (200MHz, Me$_2$SO-d$_6$) δppm: 8.68 (1H, s, 8-H), 7.88 (2H, brs, 6-NH$_2$), 6.22 (1H, d, 1'-H, J=6.0 Hz), 5.00 (1H, t, 2'-OH), 4.50 (1H, m, 3'-H), 3.90–3.85 (2H, m, 4'-Ha,b), 3.65–3.60 (2H, m, 2'-CH$_2$), 3.53 (1H, m, 2'-H), 0.95–0.88 (9H, m, t-Bu), 0.13–0.07 (6H, m, Me).

9-2 Synthesis of Compound ⑥ ($R_1$=Ac, X=Cl)

Compound ⑤ ($R_1$=TBDMS, X=Cl) (72 mg) was dissolved in acetonitrile (3 ml). Acetic anhydride (51 µl) and triethylamine (75 µl) were added, and the mixture was stirred at room temperature for 20 hours. The reaction mixture was concentrated under reduced pressure, and the residue was partitioned between saturated aqueous sodium hydrogen carbonate solution (15 ml) and ethyl acetate (20 ml). The organic layer was washed with saturated aqueous sodium chloride solution (15 ml), dried with sodium sulfate, and evaporated under reduced pressure The residue was dissolved in tetrahydrofuran (3 ml), and treated with tetrabutylammonium fluoride (1M in tetrahydrofuran, 0.2 ml) with stirring at room temperature for 10 minutes. The reaction mixture was concentrated under reduced pressure, and the residue was purified by silica gel column chromatography (MERCK silica gel 60, 30 g, eluted with a gradient of 4 to 8% methanol/chloroform) to yield Compound ⑥ ($R_1$=Ac, X=Cl) (43 mg).

Compound ⑥ ($R_1$=Ac, X=Cl)

UV (MeOH) λmax: 262 nm;
EI-MS (m/z): 329 (M+), 327 (M+);
$^1$H-NMR (200MHz, Me$_2$SO-D$_6$) δppm: 8.68 (1H, s, 8-H), 7.90 (2H, brs, 6-NH$_2$), 6.30 (1H, d, 1'-H, J=6.0 Hz), 5.28 (1H, t, 4'-OH), 4.51 (1H, m, 3'-H), 4.40–4.20 (2H, m, 2'-CH$_2$), 4.05–3.60 (3H, m, 2'-H, 4'-Ha,b), 2.04 (3H, s, Ac).

9-3 Synthesis of Compound No. 6

Compound ⑥ ($R_1$=Ac, X=Cl) (37 mg) was suspended in triethyl phosphate (1 ml). Phosphorus oxychloride (42 µl) was added at −20° C., and the mixture was stirred for one hour under an argon atmosphere. The reaction mixture was neutralized with saturated aqueous sodium hydrogen carbonate solution (15 ml) and extracted with chloroform (20 ml×3). The aqueous layer was applied to a column of DEAE-Sephadex A-25 (carbonate form, 10 ml), washed with water, and eluted with a gradient of 0 to 0.5 M aqueous ammonium carbonate solution (200 ml). The homogeneous fractions were pooled, and evaporated under reduced pressure, and the residue, i.e. Compound ⑦ ($R_1$=Ac, X=Cl), was treated with 0.5N aqueous sodium hydroxide solution (10 ml) with stirring at room temperature overnight. The reaction mixture was neutralized with 1N hydrochloric acid and then its acidity was adjusted to pH 2 by adding 1N hydrochloric acid thereto, after which it was neutralized to pH 7 with aqueous sodium hydroxide solution. The resulting solution was applied to a column of active charcoal (3 ml), washed with water, and eluted with methanol. The homogeneous fractions were pooled and evaporated to dryness under reduced pressure to yield Compound No. 6 (17 mg).

Compound No. 6

UV (H$_2$O) λmax: 262 nm;

FAB-MS (m/z): 366 (M+ = 1);

$^1$H-NMR (200MHz, D$_2$O) δppm: 8.68 (1H, s, 8-H), 6.39 (1H, d, 1'-H, J=5.8 Hz), 4.82 (1H, m, 3'-H), 4.09 (1H, dd, 4'-Ha, J=2.5, 4.5 Hz), 4.06 (1H, dd, 4'-Hb, J=2.9, 4.5 Hz), 3.90–3.85 (2H, m, 2'-CH$_2$), 3.80 (1H, m, 2'-H).

What is claimed is:

1. A 2-halogeno-oxetanocin A derivative represented by the following formula (1) or a salt thereof:

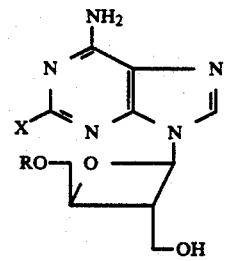
(1)

wherein X represents a fluorine atom or a chlorine atom and R represents a hydrogen atom or a phosphoric acid residue.

2. A 2-halogeno-oxetanocin A derivative represented by the following formula:

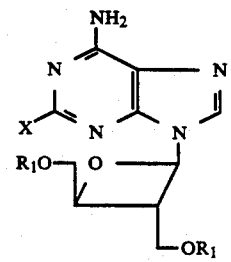

wherein X represents a fluorine atom or a chlorine atom and each R$_1$ independently represents a hydrogen atom, an acyl group or a tri(C$_1$–C$_{10}$ hydrocarbon)-silyl group, provided that a case that both the symbols R$_1$ simultaneously represent a hydrogen atom is excepted.

* * * * *